United States Patent
McIntire et al.

(10) Patent No.: US 6,689,043 B1
(45) Date of Patent: Feb. 10, 2004

(54) PRODUCTS AND METHODS FOR BRACHYTHERAPY

(75) Inventors: Gregory McIntire, West Chester, PA (US); Robert Snow, West Chester, PA (US); Edward Bacon, Audubon, PA (US); Morten Eriksen, Oslo (NO); Auden Tornes, Oslo (NO); Geraldine Cooney, Gilbertsville, PA (US); Christopher Black, Norristown, PA (US); Joel Cornacoff, Audubon, PA (US); Virginia Ann Gates, Collegeville, PA (US)

(73) Assignee: Amersham PLC, Little Chalfont (GB)

( * ) Notice: Subject to any disclaimer, the term of this patent is extended or adjusted under 35 U.S.C. 154(b) by 0 days.

(21) Appl. No.: 09/831,229

(22) PCT Filed: Nov. 5, 1999

(86) PCT No.: PCT/GB99/03668

§ 371 (c)(1),
(2), (4) Date: Jul. 23, 2001

(87) PCT Pub. No.: WO00/28554

PCT Pub. Date: May 18, 2000

Related U.S. Application Data

(60) Provisional application No. 60/107,406, filed on Nov. 6, 1998.

(30) Foreign Application Priority Data

Nov. 27, 1998 (GB) .............................. 9826121

(51) Int. Cl.[7] ........................... A61N 5/00; A61K 51/00

(52) U.S. Cl. .......................................... 600/1; 424/1.29

(58) Field of Search ................................ 600/1–8, 427, 600/431, 458; 424/1.25, 1.29; 252/478; 376/169; 206/438

(56) References Cited

U.S. PATENT DOCUMENTS

| | | | | |
|---|---|---|---|---|
| 3,351,049 A | * | 11/1967 | Lawrence | 252/478 |
| 4,323,055 A | * | 4/1982 | Kubiatowicz | 376/169 |
| 4,401,124 A | | 8/1983 | Guess | |
| 4,702,228 A | * | 10/1987 | Russell et al. | 600/8 |
| 4,869,259 A | * | 9/1989 | Elkins | 600/458 |
| 4,891,165 A | * | 1/1990 | Suthanthiran | 206/438 |
| 5,201,314 A | * | 4/1993 | Bosley et al. | 600/431 |
| 6,080,099 A | * | 6/2000 | Slater et al. | 600/8 |
| 6,168,777 B1 | * | 1/2001 | Greff et al. | 424/1.25 |
| 6,256,529 B1 | * | 7/2001 | Holupka et al. | 600/427 |

FOREIGN PATENT DOCUMENTS

| | | | |
|---|---|---|---|
| EP | 0 624 342 A | 11/1994 | |
| EP | 624342 A1 | * 11/1994 | ............ A61B/8/08 |

OTHER PUBLICATIONS

H. Lee Moffitt Cancer Center and Reseach Institute "Radioactive Seeds for Permanent Prostate Implants" Jan. 28, 2000, p. 1.

Grimm, et al. "Ultrasound–Guided Transperineal Implantation of Iodine–125 and Palladium–103 for the Treatment of Early–Stage Prostate Cancer" Atlas of the Urologic Clinics of North America, vol. 2, No. 2, Oct. 1994, pp. 113–125.

(List continued on next page.)

Primary Examiner—Eric F. Winakur
Assistant Examiner—Nikita R Veniaminov
(74) Attorney, Agent, or Firm—Li Cai

(57) ABSTRACT

Radioactive sources, preferably radioactive seeds, for use in brachytherapy comprising a radioisotope within a sealed biocompatible container, wherein at least one part of a surface of the container is roughened, shaped or otherwise treated so that it is no longer smooth. The surface treatment may enhance the ultrasound visibility of the source and/or reduce the tendency of the source to migrate once implanted in a patient's body. Preferred radioisotopes are palladium-103 and iodine-125.

5 Claims, 11 Drawing Sheets

OTHER PUBLICATIONS

Blasko, et al. "Should Brachytherapy be Considered a Therapeutic Option in Localized Prostate Cancer?" The Urologic Clinics of North America, vol. 223, No. 4, Nov. 1996, pp. 633–650.

Kahmann, F., et al., "Does intraoperative dosimetry planning for prostate permanent seed implants result in better postoperative outcome as compared to conventional pre-planning treatment?" Poster Workshops, pp. S100–S101, Friday, Sep. 22, 2000.

Stone, N., et al. "Prostate Brachytherapy: Intraoperative real time dosimetry can predict post–implant quality outcome" Poster Workshops, p. S99, Friday, Sep. 22, 2000.

Lo, Y., et al., "Prospective comparison of intraoperative real–time to post–implant dosimetry in patients receiving prostate brachytherapy" Mount Sinai Medical Center, New York, N.Y., Oct. 2000, Proceedings of the 42nd Annual ASTRO Meeting, pp. 359–360.

Sharma, R., et al., "Implementation of Real Time Dosimetric Evaluation for I–125 Prostate Brachytherapy" I.J. Radiation Oncology Biology Physics, vol. 45, No. 3 supplement 1999, p. 18.

Stock, R., et al., "Intraoperative Dosimetric Representation of the Real–Time Ultrasound–Guided Prostate Implant" Techniques in Urology, vol. 6, No. 2, 2000, pp. 95–98.

Beyer, D., et al. "Real–Time Optimized Intraoperative Dosimetry for Prostate Brachytherapy: A Pilot Study" Int. J. Radiation Oncology Biology Physics, vol. 48, No. 5, 2000, pp. 1583–1589.

Wilkinson, D., et al. "Dosimetric Comparison of PrePlanned and Or–Planned Prostate Seed Brachytherapy" Int. J. Radiation Oncology Biology Physics, vol. 48, No. 4, 2000, pp. 1241–1244.

Zelefsky, M., et al. "Postimplantation Dosimetric Analysis of Permanent Transperineal Prostate Implantation: Improved Dose Distributions with an Intraoperative Computer–Optimized Conformal Planning Technique" Int. J. Radiation Oncology Biology Physics, vol. 48, No. 2, 2000, pp. 601–608.

* cited by examiner

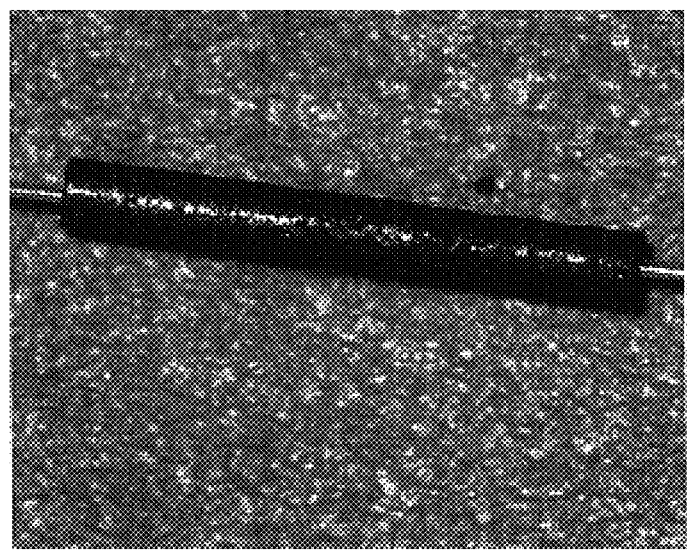
FIG.6A1
FIG.6A2

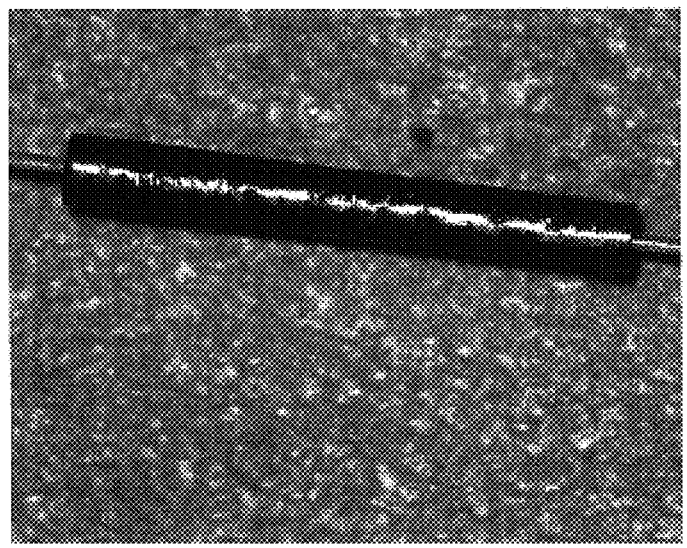
FIG.6B1
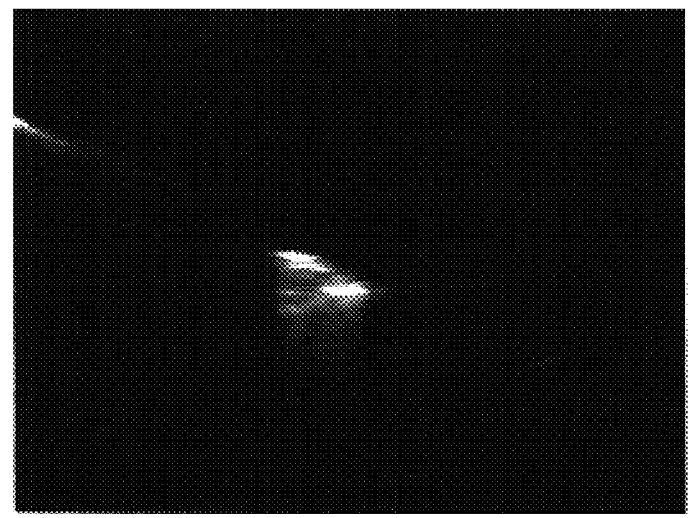
FIG.6B2

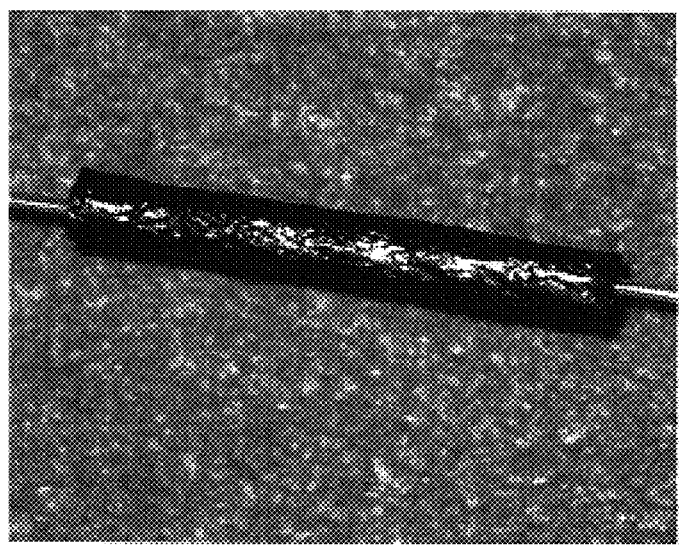
FIG.6C1
FIG.6C2

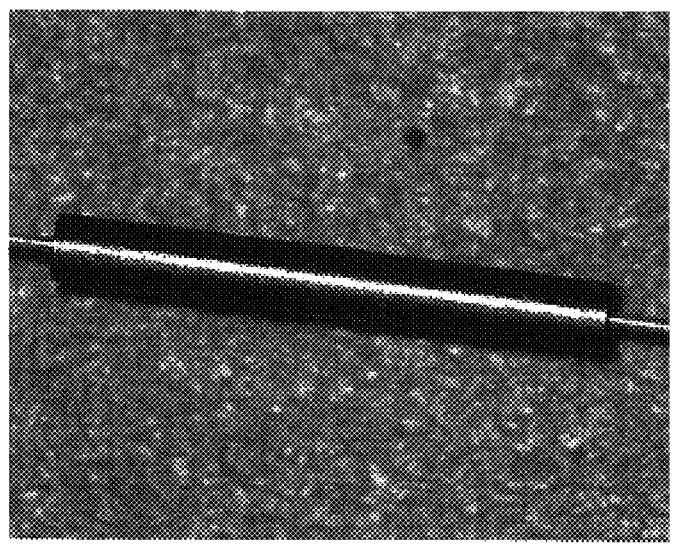
FIG.6D1
FIG.6D2

PRODUCTS AND METHODS FOR BRACHYTHERAPY

This application claims the benefit of provisional application 60/107,406 filed Nov. 6, 1998.

This invention relates to radiotherapy. More particularly, it relates to radioactive sources for use in brachytherapy, and in particular to radioactive sources with improved ultrasound imaging visibility.

Brachytherapy is a general term covering medical treatment which involves placement of a radioactive source near a diseased tissue and may involve the temporary or permanent implantation or insertion of a radioactive source into the body of a patient. The radioactive source is thereby located in proximity to the area of the body which is being treated. This has the advantage that a high dose of radiation may be delivered to the treatment site with relatively low dosages of radiation to surrounding or intervening healthy tissue.

Brachytherapy has been proposed for use in the treatment of a variety of conditions, including arthritis and cancer, for example breast, brain, liver and ovarian cancer and especially prostate cancer in men (see for example J. C. Blasko et al., *The Urological Clinics of North America*, 23, 633–650 (1996), and H. Ragde et al., *Cancer*, 80, 442–453 (1997)). Prostate cancer is the most common form of malignancy in men in the USA, with more than 44,000 deaths in 1995 alone. Treatment may involve the temporary implantation of a radioactive source for a calculated period, followed by its subsequent removal. Alternatively, the radioactive source may be permanently implanted in the patient and left to decay to an inert state over a predictable time. The use of temporary or permanent implantation depends on the isotope selected and the duration and intensity of treatment required.

Permanent implants for prostate treatment comprise radioisotopes with relatively short half lives and lower energies relative to temporary sources. Examples of permanently implantable sources include iodine-125 or palladium-103 as the radioisotope. The radioisotope is generally encapsulated in a titanium casing to form a "seed" which is then implanted. Temporary implants for the treatment of prostate cancer may involve iridium-192 as the radioisotope.

Recently, brachytherapy has also been proposed for the treatment of restenosis (for reviews see R. Waksman, *Vascular Radiotherapy Monitor*, 1998, 1, 10–18, and *MedPro Month*, January 1998, pages 26–32). Restenosis is a renarrowing of the blood vessels after initial treatment of coronary artery disease.

Coronary artery disease is a condition resulting from the narrowing or blockage of the coronary arteries, known as stenosis, which can be due to many factors including the formation of atherosclerotic plaques within the arteries. Such blockages or narrowing may be treated by mechanical removal of the plaque or by insertion of stents to hold the artery open. One of the most common forms of treatment is percutaneous transluminal coronary angioplasty (PTCA)—also known as balloon angioplasty. At present, over half a million PTCA procedures are performed annually in the USA alone. In PTCA, a catheter having an inflatable balloon at its distal end is inserted into the coronary artery and positioned at the site of the blockage or narrowing. The balloon is then inflated which leads to flattening of the plaque against the artery wall and stretching of the artery wall, resulting in enlargement of the intraluminal passage way and hence increased blood flow.

PTCA has a high initial success rate but 30–50% of patients present themselves with stenotic recurrence of the disease, i.e. restenosis, within 6 months. One treatment for restenosis which has been proposed is the use of intraluminal radiation therapy. Various isotopes including iridium-192, strontium-90, yttrium-90, phosphorous-32, rhenium-186 and rhenium-188 have been proposed for use in treating restenosis.

Conventional radioactive sources for use in brachytherapy include so-called seeds, which are smooth sealed containers or capsules of a biocompatible material, for example of metals such as titanium or stainless steel, containing a radioisotope within a sealed chamber but permitting radiation to exit through the container/chamber walls (U.S. Pat. No. 4,323,055 and U.S. Pat. No. 3,351,049). Such seeds are only suitable for use with radioisotopes which emit radiation which can penetrate the chamber/container walls. Therefore, such seeds are generally used with radioisotopes which emit γ-radiation or low-energy X-rays, rather than with β-emitting radioisotopes.

In brachytherapy, it is vital to the therapeutic outcome for the medical personnel administering the treatment to know the relative position of the radioactive source in relation to the tissue to be treated, to ensure that the radiation is delivered to the correct tissue and that no localized over or under dosing occurs. Current seeds therefore typically incorporate a marker for X-ray imaging such as a radiopaque metal (e.g. silver, gold or lead). Location of the implanted seed is then achieved via X-ray imaging, which exposes the patient to an additional radiation dose. Such radiopaque markers are typically shaped so that imaging gives information on the orientation as well as location of the seed in the body, since both are necessary for accurate radiation dosimetry calculations.

Permanent implantation of brachytherapy radioactive sources for the treatment of, for example, prostate cancer may be done using an open laparotomy technique with direct visual observation of the radioactive sources and the tissue. However, the procedure is relatively invasive and often leads to undesirable side effects in the patient. An improved procedure comprising the insertion of radioactive sources transperineally into predetermined regions of the diseased prostate gland using an external template route to establish a reference point for implantation has been proposed (see for example Grimm, P. D., et al., *Atlas of the Urological Clinics of North America*, Vol. 2, No. 2, 113–125 (1994)). Commonly, these radioactive sources, for example seeds, are inserted by means of a needle device while an external depth gauge is employed with the patient in the dorsal lithotomy position. For prostate cancer treatment, typically 50 to 120 seeds are administered per patient in a 3-dimensional array derived from multiple needle insertions of linear, spaced seeds. The dose calculation is based on this complex 3-D array, plus data on the tumour volume plus prostate volume etc.

Preferably, the insertion or implantation of a radioactive source for brachytherapy is carried out using minimally-invasive techniques such as, for example, techniques involving needles and/or catheters. It is possible to calculate a location for each radioactive source which will give the desired radiation dose profile. This can be done using knowledge of the radioisotope content of each source, the dimensions of the source, an accurate knowledge of the dimensions of the tissue or tissues in relation to which the source is to be placed, plus a knowledge of the position of said tissue relative to a reference point. The dimensions of tissues and organs within the body for use in such dosage calculations may be obtained prior to placement of the radioactive source by using conventional diagnostic imaging techniques including X-ray imaging, magnetic resonance imaging (MRI) and ultrasound imaging. However, difficulties may arise during the radioactive source placement procedure which may adversely affect the accuracy of the placement of the source if only pre-placement images are used to guide the source placement. For example, tissue volume may change as a result of swelling or draining of fluid to and from the tissue. Tissue position and orientation can change in the patient's body relative to a selected internal or external reference point as a result of for example manipulation during surgical procedures, movement of the patient or changes in the volume of adjacent tissue. Thus, it is difficult to achieve accurate placement of sources to achieve a desired dosage profile in brachytherapy using only knowledge of tissue anatomy and position that was obtained prior to the placement procedure. Therefore, it is advantageous if real-time visualisation of both the tissue and the radioactive source can be provided. A particularly preferred imaging method due to its safety, ease of use and low cost, is ultrasound imaging.

During the placement of the radioactive sources into position, a surgeon can monitor the position of tissues such as the prostate gland using, for example, transrectal ultrasound pulse-echo imaging techniques which offer the advantage of low risk and convenience to both patient and surgeon. The surgeon can also monitor the position of the relatively large needle used in implantation procedures using ultrasound. During the implantation or insertion procedure, the location of the source may be inferred to be proximal to the tip of the needle or other device used for the procedure. However, the relative location of each separate radioactive source should be evaluated subsequent to the implantation procedure to determine if it is in a desired or undesired location and to assess the uniformity of the therapeutic dose of radiation to the tissue. Radioactive sources may migrate within the tissue following implantation. However, the relatively small size of current brachytherapy radioactive sources and the specular reflection properties of their surfaces makes them very difficult to detect by ultrasound imaging techniques, especially when they are orientated in directions other than substantially orthogonal to the incident ultrasound beam. Even very small deviations from 90° relative to the incident ultrasound beam cause substantial reductions in the intensity of the echo signal.

The ultrasound visibility of conventional radioactive seeds is highly dependent upon the angular orientation of the seed axis with respect to the ultrasound inducer used for imaging. A smooth flat surface will generally act as a mirror, reflecting ultrasound waves in the wrong direction unless the angle between the sound and the surface is 90°. A smooth cylindrical structure such as a conventional radioactive seed will reflect waves in a fan shaped conical pattern spanning a considerable spatial angle but will only give strong ultrasound reflections when imaged at an angle very close to 90°. One way of improving the ultrasound visibility of conventional radioactive seeds is therefore to reduce the angular dependence of the reflected ultrasound.

There is therefore a need for radioactive sources for use in brachytherapy with improved ultrasound imaging visibility, and in particular for sources where the dependence of visibility on the angular orientation of the axis of the source with respect to the ultrasound transducer is reduced.

Ultrasound reflections may be either specular (mirror-like) or scattered (diffuse). Biological tissue typically reflects ultrasound in a scattered manner, whilst metallic devices tend to be effective reflectors of ultrasound. Relatively large smooth surfaces such as those of needles used in medical procedures reflect sound waves in a specular manner.

Efforts have been made to enhance the ultrasound visibility of relatively large surgical apparatus, such as surgical needles, solid stylets and cannulae by suitable treatment of their surfaces such as roughening, scoring or etching. Thus, U.S. Pat. No. 4,401,124 discloses a surgical instrument (a hollow needle device) that has a diffraction grating inscribed on the surface to enhance the reflection coefficient of the surface. Sound waves that strike the grooves are diffracted or scattered as secondary wave fronts in many directions, and a percentage of those waves are detected by the ultrasound transducer. The diffraction grating is provided for use at the leading edge of a surgical instrument for insertion within a body or for use along a surface of an object the position of which is to be monitored while in the body.

U.S. Pat. No. 4,869,259 discloses a medical needle device that has a portion of its surface particle-blasted to produce a uniformly roughened surface that scatters incident ultrasound such that a portion of the scattered waves is detected by an ultrasound transducer.

U.S. Pat. No. 5,081,997 discloses surgical instruments with sound reflective particles imbedded in a portion of the surface. The particles scatter incident sound, and a portion is detected by an ultrasound transducer.

U.S. Pat. No. 4,977,897 discloses a tubular cannula device comprising a needle and an inner stylet in which one or more holes are cross-drilled perpendicular to the axis of the needle to improve ultrasound visibility. The solid inner stylet may be roughened or scored to enhance the sonographic visibility of the needle/stylet combination.

WO 98/27888 describes a echogenically enhanced medical device in which a print pattern mask of non-conductive epoxy-containing ink is transfer-coated to the surface of the device, flash dried, and then thermally crosslinked. Portions of the needle not protected by the mask are removed by etching in an electropolishing step to leave a pattern of substantially square depressions in the bare metal, and the ink masked is removed with a solvent and mechanical scrubbing. The depressions provide the device with enhanced echogenicity under ultrasound.

U.S. Pat. No. 4,805,628 discloses a device which is inserted or implanted for long-term residence in the body, which device is made more visible to ultrasound by providing a space in the device which has a substantially gas impermeable wall, such space being filled with a gas or mixture of gases. The invention is directed to IUD's (intrauterine devices), prosthetic devices, pacemakers, and the like.

McGahan, J. P., in "Laboratory assessment of ultrasonic needle and catheter visualization." JOURNAL OF ULTRASOUND IN MEDICINE, 5(7), 373-7, (July 1986) evaluated seven different catheter materials for their sonographic visualisation in vitro. While five of the seven catheter materials had good to excellent sonographic detection, nylon and polyethylene catheters were poorly visualised. Additionally, various methods of improved needle visualisation were tested. Sonographic needle visualisation was aided by a variety of methods including either roughening or scoring the outer needle or inner stylet and placement of a guide wire through the needle.

However, none of the above-mentioned prior art discloses or suggests methods for improving the ultrasound visibility of radioactive sources for use in brachytherapy, including the relatively much smaller radioactive sources or seeds for use in permanent implants, nor the need to provide improved ultrasound visibility of such sources. Indeed, there is a bias in the brachytherapy field against changing the seed capsule design, since it has been essentially unchanged and has continued to be commercially successful for over 20 years, together with the fact that any such change may have Regulatory or nuclear safety implications, and would hence typically be avoided. In addition, any such change could be viewed as increasing the liklihood of problems with the seeds 'sticking' in needles etc., i.e. it is viewed as highly desirable that the seeds move smoothly within needles, cannulae etc. "Sticking" of seeds within loading devices is a known problem for clinicians and can present a safety risk. Thus, if undue pressure is applied to move a stuck seed, it is known that the seed capsule may rupture with consequent radioactive release, contamination etc. Hence, there is a bias in the art towards making seeds smoother (or at least having less friction) rather than seemingly the other way round.

Once implanted, seeds are intended to remain permanently at the site of implantation. However, individual seeds may on rare occasions migrate within a patient's body away from the initial site of implantation or insertion. This is highly undesirable from a clinical perspective, for example as it may lead to underdosing of a tumour or other diseased tissue and/or exposure of healthy tissue to radiation. There is therefore also a need for radioactive sources for use in brachytherapy which show a reduced tendency to migrate within a patient's body when compared to conventional brachytherapy seeds.

According to one aspect of the present invention there is therefore provided a radioactive source for use in brachytherapy comprising a radioisotope within a sealed biocompatible container, wherein at least one part of a surface of the container is roughened, shaped or otherwise treated such that it is no longer smooth. The surface treatment may enhance the ultrasound visibility of the source and/or reduce the tendency of the source to migrate once implanted in a patient's body.

Suitable radioisotopes for use in the radioactive brachytherapy sources of the invention are known in the art. Particularly preferred radioisotopes include palladium-103 and iodine-125.

Suitable carriers for the radioisotope within the biocompatible container may comprise materials such as plastics, graphite, zeolites, ceramics, glasses, metals, polymer matrices, ion-exchange resins or other, preferably porous materials. Alternatively, the carrier may be made of metal, e.g. silver or may comprise a layer of metal plated onto a suitable substrate. Suitable substrate materials include a second metal such as gold, copper or iron, or solid plastics such as polypropylene, polystyrene, polyurethane, polyvinylalcohol, polycarbonate, Teflon™, nylon, delrin and Kevlar™. Suitable plating methods are known in the art and include chemical deposition, sputtering, ion plating techniques, electrodeless-plating and electrodeposition.

The carrier material may be in the form of a bead, wire, filament or rod. Such carrier materials may be encapsulated in a hollow sealed container, for example a metal container, to provide a sealed source or "seed", or the carrier may be coated with an electroplated shell, for example a layer of a metal such as silver or nickel. The radioisotope may be physically trapped in or on the carrier, for example by adsorption, or may be chemically attached to it in some way. Alternatively, the source may comprise a hollow sealed container directly encapsulating the radioisotope without the need for a carrier.

Suitable biocompatible container materials include metals or metal alloys such as titanium, gold, platinum and stainless steel; plastics such as polyesters and vinyl polymers, and polymers of polyurethane, polyethylene and poly(vinyl acetate), the plastics being coated with a layer of a biocompatible metal; composites such as composites of graphite, and glass such as matrices comprising silicon oxide. The container may also be plated on the outside with a biocompatible metal, for example gold or platinum. Titanium and stainless steel are preferred metals for such containers, especially titanium.

The radioisotope may also be incorporated into a polymer matrix, or a plastic or ceramic composite, and/or may form part of a container wall. For example, if a metal alloy is used to form a container, then a component of the alloy may be a suitable radioisotope. If a container is made from a composite material, a component of the composite may be a suitable radioisotope.

The source should be of an overall size and dimensions suitable for its intended use. For example, the overall dimensions are preferably such that the source can be delivered to the treatment site using conventional techniques, for example using a hollow needle or a catheter. Seeds for use in the treatment of prostate cancer are, for example, typically substantially cylindrical in shape and approximately 4.5 mm long with a diameter of approximately 0.8 mm, such that they may be delivered to the treatment site using a hypodermic needle. For use in the treatment of restenosis, a source should be of suitable dimensions to be inserted inside a coronary artery, for example with a length of about 10 mm and a diameter of about 1 mm, preferably a length of about 5 mm and a diameter of about 0.8 mm, and most preferably with a length of about 3 mm and a diameter of about 0.6 mm. Sources for use in the treatment of restenosis are typically delivered to the treatment site using conventional catheter methodology. The sources of the invention may also be substantially spherical in shape.

The sources of the invention may be used as permanent implants or for temporary insertion into a patient. The choice of radioisotope and type of source, plus the method of treatment used, depends in part on the condition to be treated.

As used herein, the term "roughened, shaped or otherwise treated" means a surface or part surface which is not smooth and polished as in regular or conventional brachytherapy sources but which comprises irregularities or discontinuities of some kind. The irregularities or discontinuities may be arranged in a regular pattern or may be random, or there may be present a mixture of random and regular regions. The irregularities or discontinuities may take the form of grooves, scratches, abrasions, depressions or the like incised, pressed, stamped, etched or otherwise scored into a surface. The irregularities or discontinuities may also take the form of ridges, bumps, undulations or the like upstanding from a surface.

If a source with improved ultrasound visibility is required, the roughening, shaping or other treatment should be over a sufficient portion of the surface of the container that the scattering of ultrasound by the source is substantially omnidirectional. The roughening, shaping or other treatment may occur over substantially the entire surface of the container, at one or both ends, in the centre or over any other portion of the surface. Preferably, the roughening, shaping or other treatment is such that the source will be visible to ultrasound in substantially all orientations relative to the incident beam.

For improved ultrasound visibility, the size of the irregularities or discontinuities on the surface of the containers (such as rods, spheroids, canisters, seeds and the like) should be such that the ultrasound imaging visibility of the sources is improved over that of a similar source with a smooth surface. Preferably, each individual irregularity reflects and/or scatters ultrasound in an omnidirectional manner. Typically, the irregularities will be of an amplitude up to approximately one quarter of a wavelength of the ultrasound involved in water. At an ultrasound frequency of 7.5 MHz, this is about 50 μm for example 40–60 μm. Depending on the frequency of the ultrasound, amplitudes of about 30 to about 90 μm may be suitable. Within this size range, larger irregularities are preferred due to an increase in reflected energy. Lower amplitudes, for example below about 20 μm, may not provide significant enhancement of ultrasound visibility.

The roughening, shaping or other treatment may take the form of production of grooves, depressions, scratches or the like on a surface of the container. The grooves etc may be arranged randomly on the surface or in more regular patterns, for example in geometric shapes and patterns such as squares and circles, or as lines running substantially parallel or perpendicular to an axis of the source, or in a helical arrangement. Preferably, the grooves etc are not arranged in a highly repeating pattern with more than 1 repeat per quarter wavelength as such patterns may act as optical gratings and lead to a loss of omnidirectionality in the echo return. Suitable roughening, shaping or other treatment will depend in part on the exact size and shape of the radioactive source concerned, and can be readily determined using trial and error experiments.

Preferably, the irregularities or discontinuities are in the form of a helical groove (e.g. with a sinusoidal profile) on the surface of the container. The pitch of the helix may be chosen to give first order maxima in the intensity of the reflected ultrasound at certain specific angles with respect to the orthogonal orientation. For example, for a conventional radioactive seed 4.5 mm long and 0.8 mm in diameter, a pitch of about 0.6 mm will give a maximum at 10° from orthogonal with 7.5 MHz ultrasound, whilst a pitch of about 0.3 mm will give a maximum at 20° from orthogonal. For such a seed the depth of the groove from peak to bottom should be approximately 40 to 60 μm. The spacing of repetitive grooves along a source's axis should not be too close, otherwise a minimum of ultrasound scattering may occur at angles close to 90° (i.e. orthogonal).

Preferably, the source will comprise a radiopaque substance, for example silver or another metal, such that the sources may be visualised using X-ray imaging techniques in addition to ultrasound imaging.

Preferred sources of the invention are sources comprising a metal container or capsule encapsulating a radioisotope, with or without a carrier, which can be visualised by both ultrasound and X-ray imaging techniques.

One advantage of using the sources of the invention in brachytherapy is that the ultrasound signal and image may be read, measured and analysed by suitable computer software sufficiently quickly to allow a physician to plan real-time dosimetry. This is advantageous from a clinical view point for both patient and medical personnel. However, the sources of the invention may be used in processes involving any type of dosimetry mapping that uses information obtained due to the ultrasound visibility of the sources.

In addition, a physician may use the same imaging technique, i.e. ultrasound, already in place during surgery to confirm both organ (e.g. prostate) position and size, and source placement. This could enable a physician to calculate if additional sources need to be inserted, for example in situations where the dose pattern needs to be recalculated based on the "real" position of the seeds.

The radioactive sources of the invention may be supplied within a substantially linear biodegradable material, for example as in the product RAPIDStrand™ available from Medi-Physics, Inc. of Illinois, U.S.A. Preferably the sources are evenly spaced (e.g. 10 mm apart in RAPIDStrand™) to permit more even/uniform radiation dosimetry and the dimensions of the array are such that the whole can be loaded into a needle for administration to a patient. The biodegradable material may be a suture or a suitable biocompatible polymer.

The roughened, shaped or otherwise treated surface of a source of the invention may be produced by a variety of different methods. In a further aspect of the invention, there is provided a method for increasing the ultrasound visibility of a radioactive source for use in brachytherapy comprising a radioisotope and a sealed biocompatible container, the method comprising roughening, shaping or otherwise treating a surface or part of a surface of the container to thereby provide irregularities or discontinuities of dimensions and arrangement effective to enhance reflection of ultrasound to facilitate detection thereof.

For example, if the source comprises a radioisotope encapsulated in an essentially cylindrical container or an encapsulating material, then the outer surface of the container or encapsulating material may be roughened or shaped by forcing the source through a ridged or serrated dye or a threading device to impart grooves on the surface. A similar effect may be produced by milling. The surface may also be roughened as a result of mechanical friction, for example by use of a wire brush or a file, or a suitable grade of sandpaper, e.g. a coarse grade. The outer surface may also be etched, for example using a laser or water-jet cutter, or by electrolytic etching. Blasting, for example sand blasting, may also be used. Blasting may be done dry, or wet as in water-jet blasting.

If the source comprises an electroplated support, the electroplating process itself may lead to a sufficiently roughened surface for the purpose of the invention.

Manufacture of radioactive seeds comprising a radioisotope inside a sealed metal or metal alloy container usually involves the provision of a suitable metal tube, one end of which is sealed for example by welding to form a canister. The radioisotope is then introduced into the canister and the other end also sealed by for example welding to provide a sealed source or seed. Alternatively, a container or canister may be formed by stamping in a press from a core of metal or by casting, moulding or forming a core of molten metal, or by machining or drilling a solid core stock of metal, or by melting and reforming and solidifying metal stock or by fastening a cap to the end of a tube by means such as welding or threading, or by use of heat to expand and then contract the cap on cooling. The outer surface of the container may be roughened, shaped or otherwise treated at any stage of the manufacturing process. For ease of manufacture, the roughening, shaping or other treatment process preferably occurs before loading of the container with the radioisotope, more preferably on the non-radioactive metal tube before sealing of either end, and most preferably on a long section of metal tubing before it is cut into short segments suitable for use in forming canisters. The roughening, shaping or other treatment process should not be such that the integrity of the container is compromised. Preferably, the thickness of the container wall is maintained whilst the overall shape after the treatment process is such that the surface is no longer smooth.

In a still further aspect of the invention, there is provided a method for the preparation of a radioactive source comprising a radioisotope and a biocompatible sealed container at least one part of the surface of which is roughened, shaped or otherwise treated so that it is no longer smooth, the method comprising roughening, shaping or otherwise treating an exterior surface or part of an exterior surface of the biocompatible container of the source to thereby provide irregularities or discontinuities in the exterior surface.

In a still further aspect of the invention, there is provided a further method for the preparation of a radioactive source comprising a radioisotope and a sealed biocompatible container at least one part of the surface of which is roughened, shaped or otherwise treated so that it is no longer smooth, the method comprising
(i) roughening, shaping or otherwise treating a surface or part of a surface of a biocompatible container material to provide irregularities or discontinuities of dimensions;
(ii) loading a radioisotope into the biocompatible container material of step (i); and
(iii) sealing the biocompatible container.

For example, a suitable thin-walled metal tube such as a titanium metal tube may be mechanically deformed before insertion of the radioactive material and welding of the ends to form a sealed source. A smooth helical groove may be produced on both the inner and outer surfaces of the tube without affecting the thickness of the wall by use of a suitable crimping process. A support tool of cylindrical shape and with outer threads of a suitable pitch and depth may first be inserted into the metal tube. The support tool should fit tightly within the tube. A crimping tool may then be applied forcefully to the outer surface of the tube. The shape of the crimping tool should match that of the support tool. The crimping tool may consist of two or more parts, each part covering a different sector of the tube's surface. Following the crimping operation, the support tool may be removed by simply twisting due to its helical threaded shape.

One or more helical grooves may also be produced by gently pressing a sharp metal edge to the surface of a container while the container is rolled over a solid surface at a slight angle, either before or after the container is sealed to form a radioactive source.

If improved ultrasound visibility of a source is desired, alternatively or additionally to roughening, shaping or treatment of the outer surface, the inner surface of the container may be roughened, shaped or otherwise treated prior to introduction of the radioisotope. For example, a non-uniform or roughened surface inside a container may be introduced by means of a tap to create helical or screw threads on the inside of the container. The tap may gouge, score or auger out a thread pattern as it is turned into the container. The spacing of the threads on the inside of a container may be set at any desired dimension obtainable by tapping the inside of the container. The tapping may be done before one end is sealed (i.e. on a tubular precursor to the container) or after one end is sealed (i.e. on a can). Preferably, the tubing is scored before it is sealed at one end.

If the inner surface of a container is roughened, shaped or otherwise treated, the overall thickness of the container wall should not be so great that no ultrasound penetrates to the interior of the container and is reflected therefrom. Suitable thicknesses may be readily determined by experimentation. A thickness of the container wall of up to about 0.1 mm is suitable.

The thickness of the wall of a container encapsulating a radioisotope is dependent upon at least the energy of the radioisotope and the nature of the carrier. For example, conventional $^{125}$I sources use 50 $\mu$m thick titanium cylinders for containment which are sufficient to block beta particles emitted by the $^{125}$I while letting enough gamma rays and low energy X-rays through for therapeutic impact. However, if an aluminum container were used, the wall thickness would need to change in order to adequately capture any beta particles emitted. Correspondingly, if a polymeric container were used, it would need to be coated, for example with a titanium oxide "paint" or be plated with a metal to modify or block beta particle emissions if the plastic itself did not capture them. Higher energy sources may be used with thicker carriers than lower energy sources.

The number of helical or spiral ridges, threads, grooves or the like on an inner or outer surface of a container may be, for example, in the range from about 1 to about 100 per mm of length of the container body.

The tube or container may be incised with at least one ridge, thread or groove pattern and optionally with more than one such pattern of different advancing spiral or helical threads which may be in the same or opposite sense of handedness. The thickness or depth of each such ridge, thread or groove may vary from about 1 $\mu$m to about half the thickness of the container wall if desired. Two or more ridges, threads or grooves of different spacings, different handedness, and/or different thicknesses or depths may be tapped into the container to give a wide variety of scoring patterns on the inside surface thereof or incised onto the outer surface of the container to give a wide variety of scoring patterns on the outside thereof.

The thickness of the container wall may preferably be within the specifications set for conventional brachytherapy radioactive sources and seeds, or it may be selected as the optimum useful in brachytherapy by clinical experimentation. Optionally, the container wall may be thicker than finally desired at the start of the roughening, shaping or other treatment procedure, and excess thickness may be removed during the procedure, for example during tapping of the inside of the container.

The roughening or shaping on the outer surface of a container according to the invention may take the form of serrations on the surface. The serrations may be in the form of teeth, steps, notches or projections on the surface of the container. Such serrations may be grouped on part of the surface to form a cluster, and/or may be set in rows on part of the surface. A serrated tooth has one edge subtended from the surface that is longer than a second edge that is also subtended from the surface, the two such edges meeting at a common point or peak. The direction of the serrated tooth is defined as the direction in the plane of the shorter edge. In another aspect, the edges of the teeth may be of similar length, and the teeth may be substantially symmetrical in two-dimensions. In another aspect, the teeth may be conical, pyramidal or trigonal or of other geometric shape wherein a point is achieved. The teeth may be of uniform or non-uniform size, and the teeth may comprise more than one serrate. When more than one set of serrations is present, they should be spaced apart on the surface of the source and should not all run in the same direction. Preferably, there will be two sets of serrations on opposite sides of a source, and more preferably running in opposite directions.

The roughening, shaping or other treatment of an outer surface of the source of the invention may reduce the tendency of the sources to migrate or move once implanted inside a patient when compared to conventional smooth seeds. Serrations on two or more portions of the surface of a source are particularly suitable in this respect. Such serrations may also lacerate tissue during implantation, resulting in the formation of scar tissue which may also help serve to keep the implanted source in place. Preferably, the roughening, shaping or other treatment is sufficient to reduce the tendency of a source to migrate but is not such that the sources cannot be delivered to the treatment site using conventional methodology and handling techniques. A suitable degree of roughening etc. may be found by trial and error experimentation.

If the source comprises a container comprising a composite material, then the outer surface of the container may be roughened by exploiting differences in the physical properties of the materials comprised in the composite. For example, if the composite comprises a blend of polymers that are phase separated in the blend and have different solubility properties in a particular solvent, then the surface may be roughened by exposing it to that solvent and thereby causing part of the blend to dissolve. Alternatively, if the composite comprises a polymer and a salt, then exposure to a suitable solvent may dissolve the salt but not the polymer and thereby cause roughening of the surface.

A container comprising a polymeric or ceramic could be rendered "rough" by entraining particles of water soluble materials within the material of the container. For example, particles of sodium chloride which are substantially insoluble in most polymer melts could be entrained in a polymeric container. Upon exposure to water or simply by placement within the tissue of interest, the sodium chloride particles may dissolve leaving a "rough" surface to the container. The resulting hyperosmotic effect around the source may also elicit a physiological response, which might help serve to anchor the source to a greater degree than normal and so avoid subsequent movement of the source.

A ceramic composite container could be prepared from two or more different but compatible ceramic materials such that exposure of the container to acid or base could selectively dissolve one or more of the carrier components so leading to a suitably roughened surface. For example, a combination of aluminum oxide and titanium oxide could afford selective dissolution in strongly basic solutions as aluminum is soluble at very high pH whilst titanium passivates and does not dissolve in such media.

Alternatively, a container may be exposed to a corrosive solution such that the surface is corroded in an uneven way to lead to a suitably roughened surface. For example, stainless steel is susceptible to crevice corrosion by action of chloride ion in an oxidizing environment at lower pH values.

Any conventional brachytherapy sources may be roughened, shaped or otherwise treated using the method of the invention to improve their ultrasound imaging visibility. For example, the ultrasound visibility of the radioactive seeds disclosed in U.S. Pat. No. 5,404,309, U.S. Pat. No. 4,784,116 and U.S. Pat. No. 4,702,228 could be improved. These seeds comprise a capsule and two radioactive pellets separated by a radiopaque marker within the capsule. The opaque marker imparts detectability by X-ray imaging of the seeds. Roughening of the surface of such capsules could be achieved for example by abrasive filing or scratching of the surface. Furthermore, abrasive roughening could be done exclusively in the region of the capsule proximal to the opaque marker in each design to thereby impart enhanced ultrasound detectability to the capsule in addition to detectability by X-ray imaging. The region of the capsule that is proximal to the radioactive pellets may not be roughened, so that the thickness of the wall of the capsule remains substantially uniform around the radioactive pellets. The dose of radiation received from such partially roughened capsule when implanted in a patient may therefore be substantially unchanged from the dose of radiation from a completely unroughened conventional capsule. Calculation and administration of the dose of radiation may then be independent of the depth or extent of the surface roughening in the region of the opaque marker. Likewise, roughening in the region of the marker may be done in depths and to degrees which may change the thickness of the capsule wall without substantially altering the profile of radiation dose received by the patient.

In a further aspect, the invention also provides a method of treatment of a condition which is responsive to radiation therapy, for example cancer, arthritis or restenosis, which comprises the temporary or permanent placement of a radioactive source comprising a radioisotope within a sealed biocompatible container, wherein at least one part of a surface of the container is roughened, shaped or otherwise treated to thereby provide irregularities or discontinuities, at the site to be treated within a patient for a sufficient period of time to deliver a therapeutically effective dose.

The invention will be further illustrated, by way of example, with reference to the following Drawings.

FIGS. 5 and 6A to D are ultrasound images of a metal wire and metal tubes roughened using embodiments of the methods of the invention.

Figure 7A:
Figure 7B:
Figure 7C:
Figure 7D:
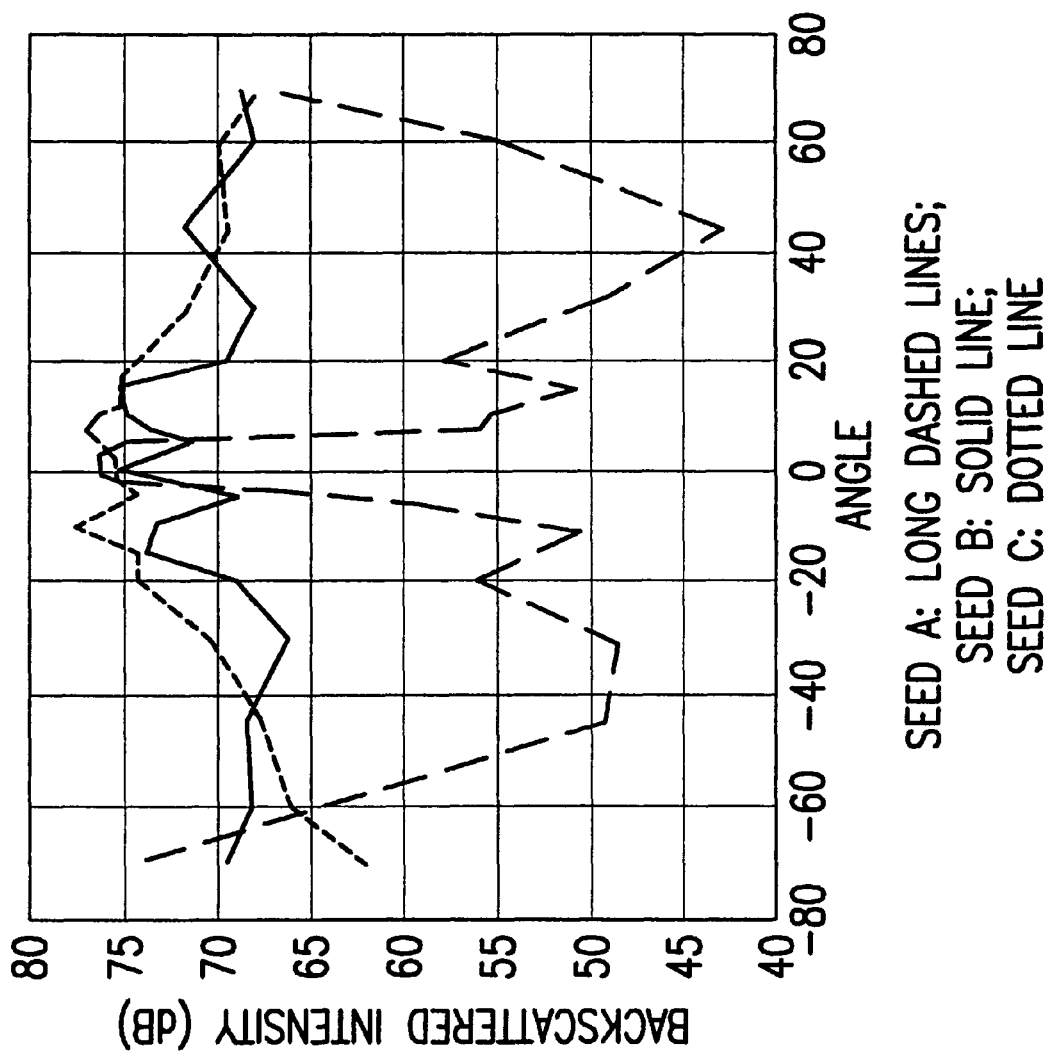

FIG. 7A is a picture of a conventional titanium seed casing and FIGS. 7B and 7C are pictures of similar seed casings roughened using embodiments of the method of the invention. FIG. 7D shows in graphical form the backscattered intensity as a function of the angle of the seed axis in relation to the ultrasound beam for the seed casings of FIGS. 7A to C.

Figure 8:
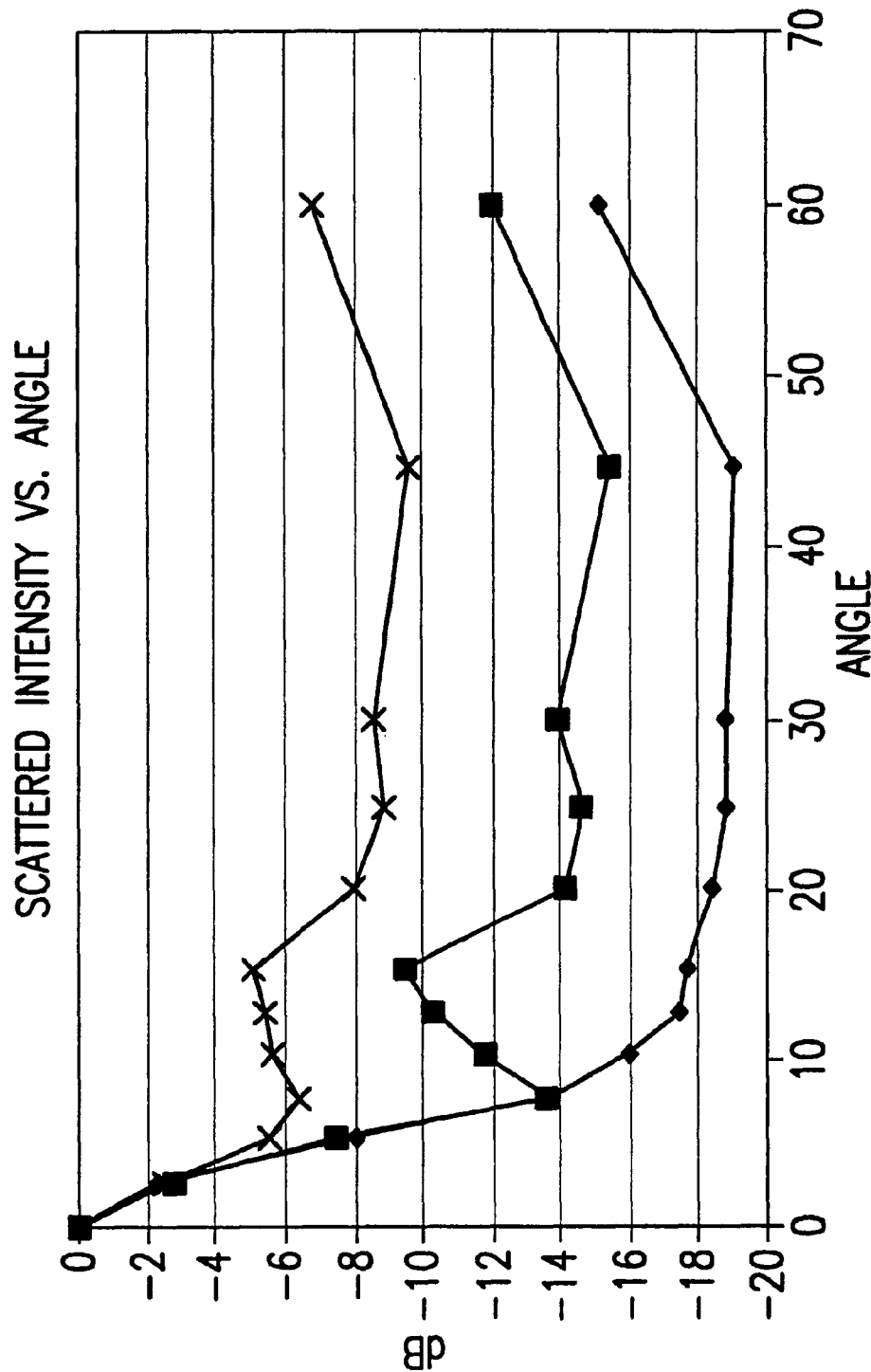

FIG. 8 shows in graphical form the backscattered intensity as a function of the angle of the seed axis in relation to the ultrasound beam for a conventional seed casing and two seed casings modified according to the invention.

Figure 1:
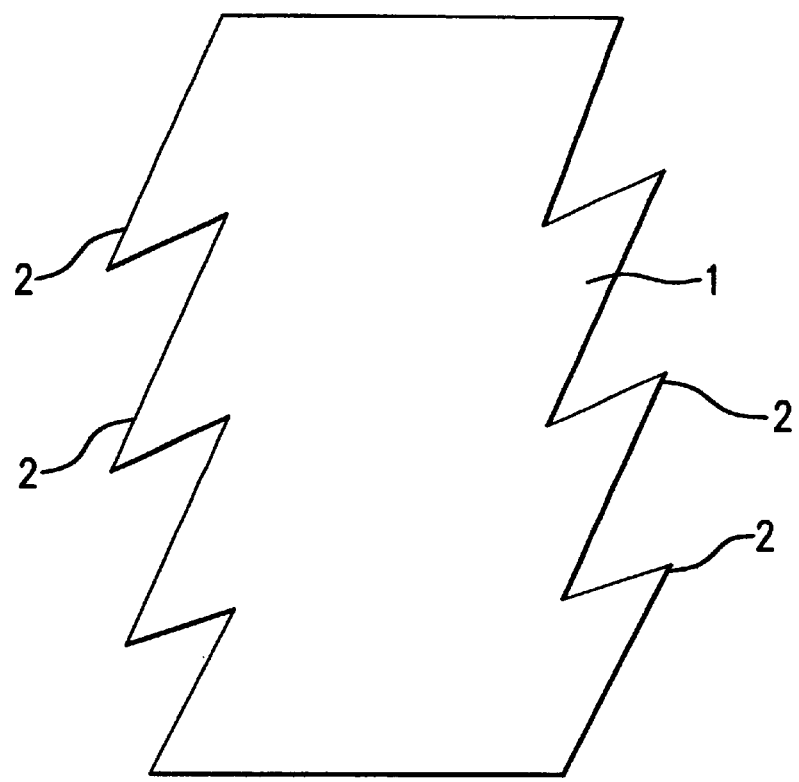
FIG. 1 illustrates one embodiment of a radioactive source according to the invention.

FIG. 1 is a schematic illustration of part of a source 1 with serrated edges 2, the serrations running in opposite directions on opposite edges.

Figure 2:
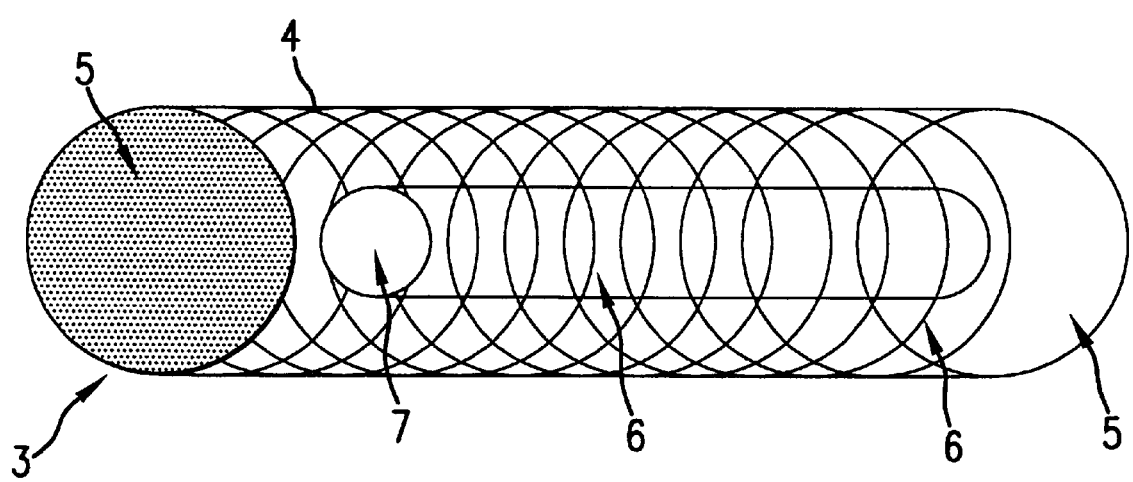
FIG. 2 illustrates another embodiment of a radioactive source according to the invention.

FIG. 2 is a schematic illustration of a sealed source 3 according to one embodiment of the invention. The source comprises a metal, for example titanium, container 4 sealed at both ends 5. The inside and/or outside on the container has a screw thread 6 etched thereon. The container contains a silver rod 7 coated with a layer of $^{125}$I-containing silver iodide. The silver rod 7 is detectable by X-ray imaging techniques.

Figure 3:
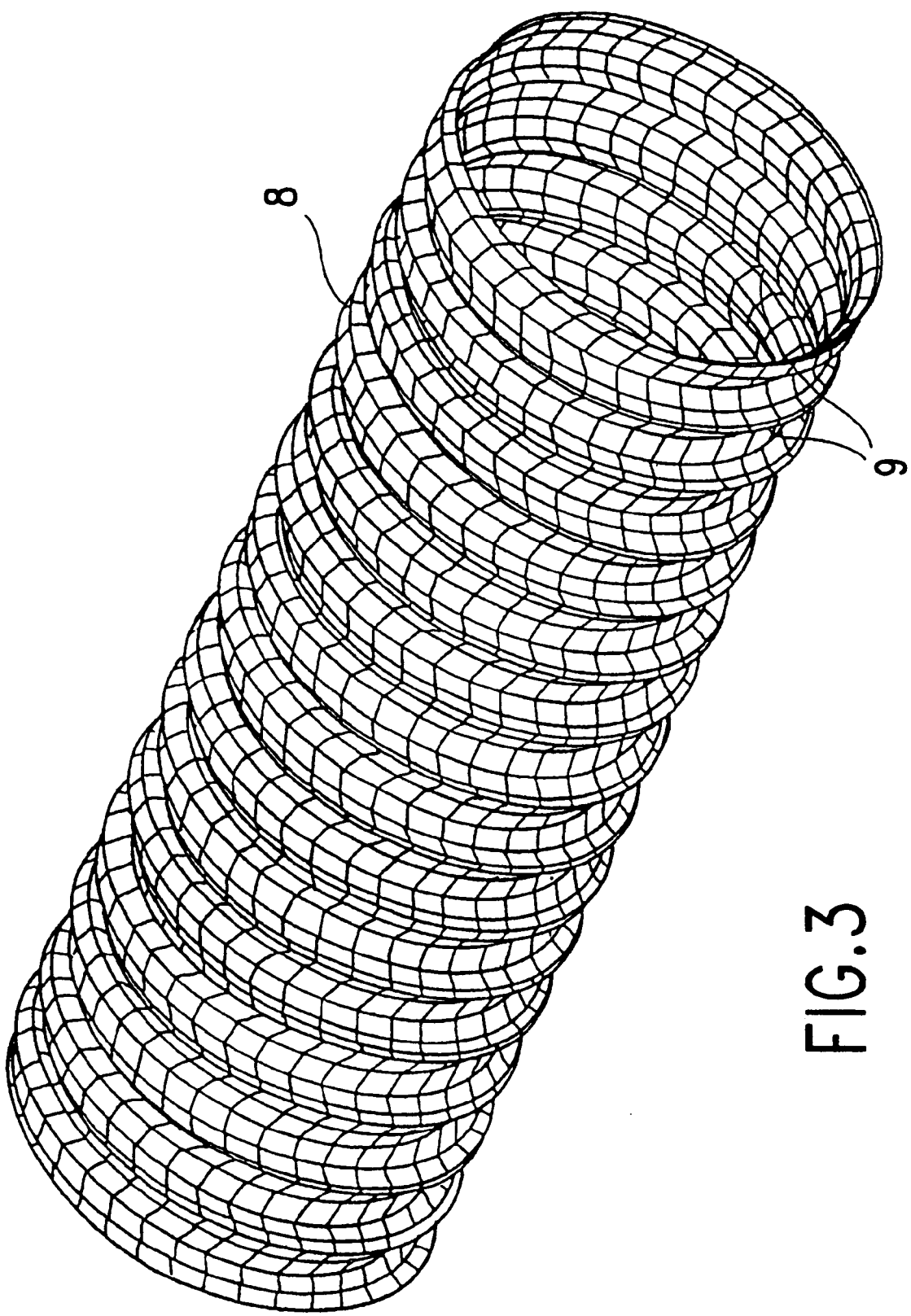
FIG. 3 illustrates a metal tube suitable for use in the production of one embodiment of a radioactive source according to the invention.

FIG. 3 illustrates a metal (e.g. titanium) tube 8 which has been subjected to a crimping operation to form helical groves 9 on the outside and inside thereof. Such a tube is suitable for use in the production of a sealed radioactive source according to the invention.

Figure 4:
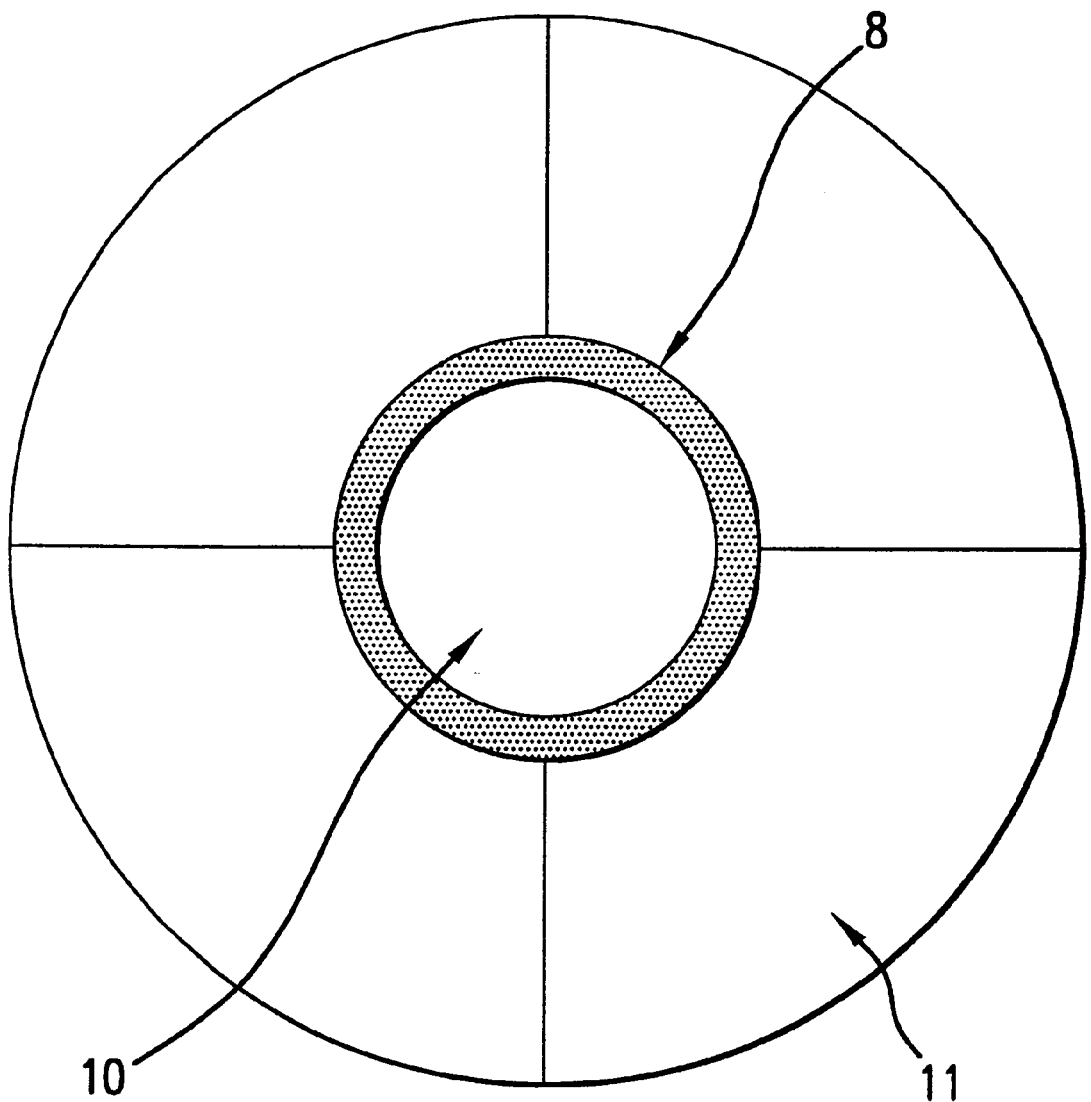
FIG. 4 illustrates a cross-sectional view of the metal tube of FIG. 3 during the crimping operation.

FIG. 4 illustrates in schematic form a cross section through the metal tube 8 of FIG. 3 during the crimping operation. The tube is crimped between a support tool 10 and a crimping tool 11, made up of four different segments.

FIGS. 5 and 6A to D are ultrasound images which are discussed in more detail in the following Examples.

FIGS. 7A to D and 8 will also be discussed in more detail in the Examples.

The invention will be further illustrated with reference to the following non-limiting Examples:

EXAMPLES

Example 1

A 12 mm long section of a 0.8 mm diameter copper wire was mechanically roughened using pliers with a serrated jaw, but no material was removed form the wire. The ultrasound visibility compared with that of a smooth, unroughened portion of the same wire. The results are shown in FIG. 5, which is a sample B-mode ultrasound image of the wire in a water tank obtained using a Vingmed CFM-750 scanner at 5 MHz.

Figure 5:
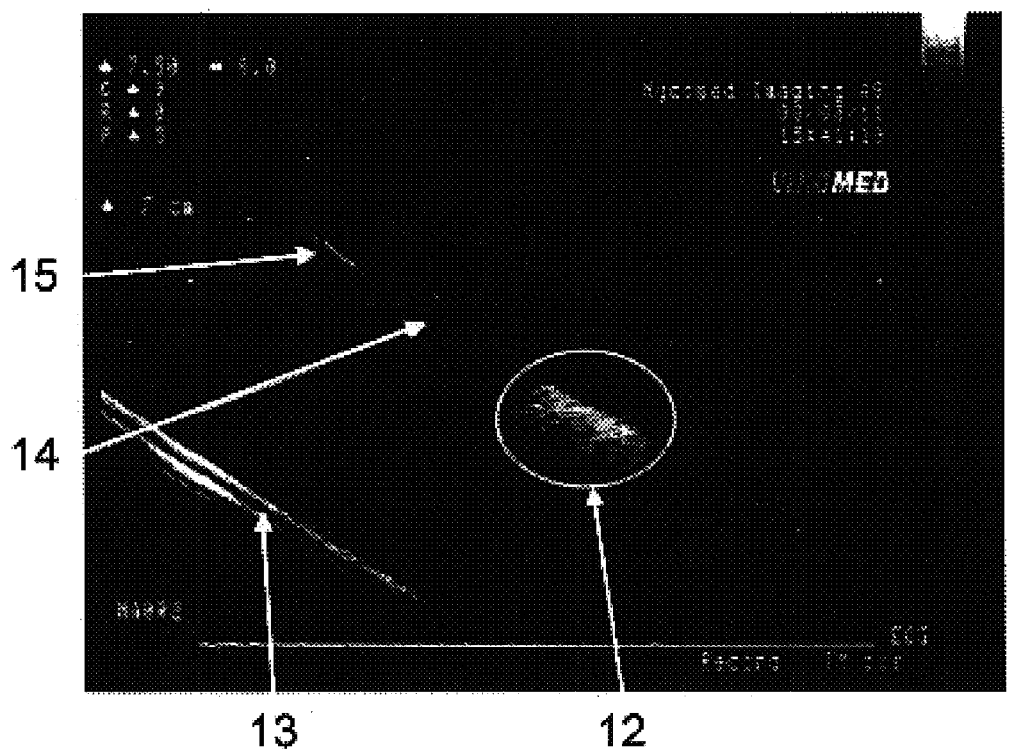

In FIG. 5, 12 is the 12 mm long roughened portion of the wire; 13 is the bottom edge of the water tank used in the experiment; 14 is a smooth portion of the wire and 15 is a specular reflection from the smooth wire section at a 90° angle to the incident ultrasound. The brightest region of the wire in the ultrasound image is the roughened portion, illustrating that the roughening of the invention greatly increases ultrasound visibility.

Similar results are obtained if the surface of a conventional titanium seed canister is roughened in the same way.

Example 2

A straight, thin (0.1 mm diameter) monofilament nylon wire was mounted in a water bath, and imaged with a Vingmed CFM-750 ultrasound scanner at 7.5 MHz. The wire was arranged to run diagonally across the image, at an angle of 45° with respect to the soundbeam direction in the centre of the image sector. This wire served as a support for pieces of titanium tubing that could be moved in and out of the central image field. The titanium tubes were those used to form conventional canisters for production of brachytherapy seeds (length 5 mm, diameter 0.8 mm, wall thickness 0.05 mm), but without welded ends and the radioactive insert. Images of pieces of tubing with different surface modifications were made in the exact same location, and without changing the geometry or the scanner instrument settings. A common feature of all imaged tube segments are diffraction artefacts at the unclosed ends. Valid comparisons of performance can thus only be made by studying the central regions of the tubes. Also, a bright halo was seen in the images behind the tubes, most probably caused by acoustic reverberations inside the tube structure.

The following surface modifications were made:
a) fine abrasive grinding, b) rough abrasive grinding, c) rough deformation with no loss of material, and d) no modifications to the original surface.

FIG. 6A to D shows the resulting ultrasound images. All modifications resulted in an improved visibility of the central portion of the seeds when compared to the non-modified case d). Best performance was observed with fine grinding, a).

Example 3

Measurement Set-up

A wide band 7.5 MHz transducer (Panametrics V320) was mounted in the measurement chamber wall. With a transducer diameter of 13 mm and a focal distance of 50 mm this transducer has an acoustic field similar to a typical phased array transducer used in clinical TRUS applications.

A brachytherapy seed was mounted on a holder which could be rotated to defined angles in relation to the direction of the ultrasound beam. The seed was glued on to the tip of a needle protruding from the specimen holder with cyanoacrylate glue so that the seed's centre of gravity coincided with the rotational axis of the holder. The angular rotation could be set with half a degree accuracy, which is of great importance given the high angular dependency of the US backscatter. The holder could also be adjusted by translation to position the seed in the focal point of the transducer and fixed throughout the experiments.

The transducer was excited with a wide band pulse from a Panametrics 5800 pulser-receiver. The received signal was acquired with a LeCroy 9310 oscilloscope and digitised. The sampled radio frequency (RF) signal (fs=50 MHz) was then transferred to a computer for further processing.

Three different seeds were tested; an unmodified seed and two different modified seeds. The unmodified seed (A) was identical to a standard seed except that it has not loaded with radioactive iodine. The dimensions of the seed were 0.8×4.2 mm and the wall thickness of the titanium tube was 50 microns. Two similar seeds were modified by gently pressing a sharp metal edge to the seed surface while the seed was rolled over a solid surface at a slight angle. The resulting deformation was one or more helical grooves running along the full length of the seed. One of the modified seeds (B) was placed on very fine sandpaper for friction during the deformation and a helical groove of 0.058 mm depth, 0.1 mm width and about 0.54 mm pitch was produced. The other modified seed (C) was placed on a thin rubber sheet during the deformation and the result was several finer helical grooves with about 0.03 mm depth and 0.2 mm groove spacing. FIGS. 7A, 7B and 7C show magnified views of the seeds A, B and C respectively. The images were transferred to an image analysis program (Optimas) for measurements of the deformations. The image processing program was calibrated using the undistorted length of the seed as a reference and several measurements of groove thickness, width and pitch were averaged for a representative characterisation of the seed surface distortion.

A series of measurements mapping the ultrasound backscatter of each of the seeds throughout the full range of incidence angles (−65 to 65 degrees) were performed. After accurate positioning at the desired angle, 10 ultrasound pulses were transmitted at a PRF of 10 Hz and the received echoes were digitised and stored. The 10 pulses were averaged coherently before further processing. Three different methods were tested for estimation of the backscattered echo intensities; a) the square of the peak amplitude, b) the integral of the signal in a 0.5 microsecond gate around the peak amplitude, and c) the integral of a bandpass filtered (5–9 MHz) version of the signal in a 1 microsecond timegate centred as in b). Method a) best represents the "brightness" of the seed in an ultrasound image, while methods b) and c) more nearly represent the overall backscattered energy. The three methods yielded very similar results for all seeds and angles and the results of method a) are used herein. Further, images of envelope detected individual scanlines at different angles were made for visualisation. These images directly represent what a small section of the image containing the seed would look like on a normal B-mode image.

The numeric results of the backscattered intensity are presented in graphical form in FIG. 7D. The intensity at normal incidence (i.e with the seed axis orthogonal to the ultrasound beam) was very similar between the different samples. For the unmodified seed A, the backscattered intensity dropped off very quickly with increasing angle away from the normal. At 10 degrees angle in either direction, the intensity had reached a minimum about 23 dB below the level of normal incidence (0 degrees). Judging from those measurements, the seed would be dramatically less visible, if visible at all, at angles exceeding ±2.5 degrees from normal incidence. The backscattered intensity increased again as the incidence angle approached 60 degrees since the tip of the seed entered the ultrasound beam and sound was reflected off the rounded seed tip.

The modified seeds B and C had a much less pronounced reduction in backscattered intensity with increasing incidence angle. The intensity did not drop more than about 10 dB for either of the two modified seeds within ±60 degrees of the incidence angle, and the seeds are therefore expected to be visible at a much larger angular range than the unmodified seed. For lower angles, variations in intensities caused by constructive and destructive interference of the sound reflected on the groves could be observed. This was more pronounced for seed B as the helical pattern here was deeper and more defined than for seed C. The dispersion of scattered energy through larger angles for the modified seeds compared to the unmodified seed did not significantly effect the backscattered intensity at normal incidence.

Example 4

The ultrasound visibility of three types of seed in a prostate phantom was investigated. The prostate phantom was a commercially available phantom and seeds were inserted in the phantom using the clinical set-up for seed implantation: i.e., B&K Panther ultrasound machine using 7.5 MHz transrectal ultrasound transducer; MMS treatment planning software; B&K hardware for seed implantation; standard 18 gauge seed-implantation needles.

Three different seed types were investigated. The reference seeds (ref) were dummy (i.e non-radioactive) seeds corresponding to the seeds commercially available from Medi-Physics, Inc. under model number 6711. Seeds A corresponded to the reference seed modified by the addition of five longitudinally spaced grooves around the central portion of each seed and seeds AC were prepared in a manner analogous to seed B of Example 3.

The seeds were implanted at a range of angles relative to the ultrasound beam (with 0° corresponding to the long axis of the seed being orthogonal to the ultrasound beam) and the ultrasound visibility of the implanted seeds was measured.

FIG. 8 shows the results for the three different types of seed. When the ultrasound beam struck a seed within the phantom with a deviation of 0°±2° (i.e.: at exactly 90° to the seed's long axis) there was little difference between the reference and the modified seeds of the invention. However, when the seeds were implanted at an angle to the ultrasound beam, the modified seeds retained their echogenicity to a much greater extent than did the reference seeds.

What is claimed is:

1. A method for the preparation of a radioactive source used in brachytherapy comprising a radioistope within a sealed biocompatible container wherein at least one part of a surface of the container is roughened, shaped or otherwise treated so that it is no longer smooth, comprising roughening, shaping or otherwise treating an exterior surface or part of an exterior surface of the biocompatible container to thereby provide irregularities or discontinuities of dimensions in the exterior surface, where the surface roughening or shaping is achieved by forcing through a ridged or serrated dye, or a threading device, milling, roughening by mechanical friction, etching, crimping, or wet or drying blasting.

2. A method for the preparation of a radioactive source used in brachytherapy comprising a radioistope within a sealed biocompatible container wherein at least one part of a surface of the container is roughened, shaped or otherwise treated so that it is no longer smooth, comprising roughening, shaping or otherwise treating an exterior surface or part of an exterior surface of the biocompatible container to thereby provide irregularities or discontinuities of dimensions in the exterior surface, where the surface roughening or shaping involves selective dissolution of one component of a composite biocompatible material.

3. A method as claimed in claim 2 wherein the composite material is a ceramic composite, a polymer blend, or a polymeric or ceramic material with soluble materials entrained therein.

4. A composition which comprises a multiplicity of radioactive sources within a substantially linear, biodegradable material, wherein the radioactive sources are for use in brachytherapy which comprises a radioisotope within a sealed biocompatible container, wherein at least one part of a surface of the container is roughened, shaped or otherwise treated to that it is no longer smooth.

5. A composition as claimed in claim 4 where the biodegradable material is semi-rigid.

* * * * *